United States Patent
Collins et al.

(10) Patent No.: US 10,258,554 B2
(45) Date of Patent: Apr. 16, 2019

(54) FLUORIDE FREE AND ANIONIC SURFACTANT FREE DENTIFRICE HAVING A HIGH MICRO EFFICACY

(75) Inventors: Michael Collins, Hazlet, NJ (US); Linh Fruge, Hillsborough, NJ (US); Barbara Hepler, South Bound Brook, NJ (US); Kimdra Smith-Webster, Williamstown, NJ (US)

(73) Assignee: Colgate-Palmolive Company, New York, NY (US)

( * ) Notice: Subject to any disclaimer, the term of this patent is extended or adjusted under 35 U.S.C. 154(b) by 165 days.

(21) Appl. No.: 13/574,100

(22) PCT Filed: Jan. 28, 2011

(86) PCT No.: PCT/US2011/022860
§ 371 (c)(1),
(2), (4) Date: Jul. 19, 2012

(87) PCT Pub. No.: WO2011/094494
PCT Pub. Date: Aug. 4, 2011

(65) Prior Publication Data
US 2012/0288453 A1    Nov. 15, 2012

Related U.S. Application Data

(60) Provisional application No. 61/299,730, filed on Jan. 29, 2010.

(51) Int. Cl.
| | | |
|---|---|---|
| *A61Q 11/00* | (2006.01) | |
| *A61K 8/00* | (2006.01) | |
| *A61K 8/34* | (2006.01) | |
| *A61K 8/36* | (2006.01) | |

(52) U.S. Cl.
CPC ............... *A61K 8/345* (2013.01); *A61K 8/36* (2013.01); *A61Q 11/00* (2013.01); *A61K 2800/30* (2013.01); *A61K 2800/5922* (2013.01)

(58) Field of Classification Search
USPC .......................................................... 424/49
See application file for complete search history.

(56) References Cited

U.S. PATENT DOCUMENTS

| | | |
|---|---|---|
| 3,957,967 A | 5/1976 | L'Orange |
| 4,943,429 A * | 7/1990 | Winston et al. ............... 424/52 |
| 5,405,604 A | 4/1995 | Hall |
| 5,885,553 A | 3/1999 | Michael |
| 5,885,554 A | 3/1999 | Michael et al. |
| 6,214,383 B1 | 4/2001 | Esch et al. |
| 6,352,711 B1 * | 3/2002 | Campbell ...................... 424/435 |
| 2003/0216423 A1 * | 11/2003 | Ulloa et al. ................... 514/290 |
| 2005/0042184 A1 * | 2/2005 | Colle et al. ...................... 424/52 |

FOREIGN PATENT DOCUMENTS

| | | |
|---|---|---|
| DE | 2430280 | 1/1976 |
| EP | 0368130 | 5/1994 |
| EP | 1001010 | 5/2003 |
| ES | 2137139 | 12/1999 |
| GB | 1232627 | 5/1971 |
| JP | S60-38321 | 2/1985 |
| JP | H02-223511 | 9/1990 |
| JP | H08-502292 | 3/1996 |
| JP | H09-510186 | 10/1997 |
| JP | H10-212220 | 8/1998 |
| JP | 2007-518828 | 7/2007 |
| JP | 2010-018551 | 1/2010 |
| RU | 2247555 | 3/2005 |
| WO | WO 96/039116 | 12/1996 |
| WO | WO 01/022930 | 4/2001 |
| WO | 2003/045344 | 6/2003 |
| WO | 2003/058633 | 7/2003 |

OTHER PUBLICATIONS

Colgate-Palmolive, 2007, "Overnight Antibacterial Mouthwash," Database Mintel GNPD AN: 648765.
Colgate-Palmolive, 2007, "Stain Prevention Mouthwash," Database Mintel GNPD AN: 708111.
Colgate-Palmolive, 2008, "Gentle Care Mouthwash," Dabase Mintel GNPD AN: 922463.
Colgate-Palmolive, 2010, "Mild Fruit Toothpaste," Database Mintel GNPD AN: 1377438.
International Search Report and Written Opinion in International Application No. PCT/US2011/022860, dated Dec. 29, 2011.
Watanabe et al., 1989, "Antimicrobial Properties and Safety of Humectants," Fragrance J. 17(2):65-73 (Abstract only in English).
Baird, et al., eds.,1996, "Control of microbial contamination in cosmetics, toiletries and non-sterile pharmaceuticals," Microbial Quality Assurance in Cosmetics, Toiletries and Non-Sterile Pharmaceuticals, Second edition, pp. 3-5 and 69-74.
Barbosa-Canovas et al., 2003, "Chapter 3: General considerations for preservation of fruits and vegetables," Handling and preservation of fruits and vegetables by combined methods for rural areas, FAO Agricultural Services Bulletin, Technical Manual.
European Patent Office, 2018, Decision Revoking the European Patent 11702565.0.
Flick, 1992, Cosmetic and Toiletry Formulations, second edition, vol. 2, p. 850.
Jungermann et al., eds., 1991, Glycerine: A Key Cosmetic Ingredient, p. 388.
Varvaresou et al., 2009, "Self-preserving cosmetics," International Journal of Cosmetic Science 31:163-175.

\* cited by examiner

*Primary Examiner* — Lezah Roberts

(57) ABSTRACT

An oral care composition and method are described in which the composition is free of an anionic surfactant and a fluoride source.

17 Claims, No Drawings

FLUORIDE FREE AND ANIONIC SURFACTANT FREE DENTIFRICE HAVING A HIGH MICRO EFFICACY

CROSS-REFERENCE TO RELATED APPLICATIONS

This application is a national stage entry under 35 U.S.C. § 371 of International Patent Application No. PCT/US2011/022860, filed on Jan. 28, 2011, which claims priority to U.S. Provisional Patent Application No. 61/299,730, filed on Jan. 29, 2010, which is are incorporated herein by reference.

BACKGROUND

The present invention relates to oral care compositions, and more particularly to compositions that do not contain fluoride ion sources and anionic surfactants. The oral care compositions comprise a pH control agent and a humectant system containing glycerin, propylene glycol, and sorbitol. Such compositions include, for example, dentifrices.

Fluoride and anionic surfactants are common components in oral care compositions. Topical administration of oral care compositions comprising fluoride and anionic surfactants are known to have beneficial effects. Fluoride ion sources and anionic surfactants also contribute to the micro efficacy of an oral care composition.

While fluoride and anionic surfactants are beneficial when used topically in an oral care composition, there are situations in which exposure to fluoride and anionic surfactants is not desired. For example, exposure to high amounts of fluoride may lead to fluorosis. The adverse effects of exposure to fluoride or anionic surfactants are particularly pronounced in children.

Thus, there is an ongoing need for new oral care compositions that do not contain fluoride or anionic surfactants, and which have a high micro efficacy.

SUMMARY

In some embodiments, the present invention provides oral care compositions free of anionic surfactants and fluoride. In some embodiments, the oral care composition comprises glycerin, propylene glycol, and sorbitol.

In another aspect, the present invention includes a method of providing oral health benefits to an oral surface comprising contacting the oral surface with an oral care composition comprising glycerin, propylene glycol, sorbitol, and citric acid, wherein the oral care composition is free of anionic surfactants and fluoride ion sources.

DETAILED DESCRIPTION

Embodiments of the present invention provide compositions and methods for administration to, or use with, a human or other animal subject. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, sensory, decorative, or cosmetic benefit without undue adverse side effects (such as toxicity, astringent taste, irritation, and allergic response) commensurate with a reasonable benefit/risk ratio. The following definitions and non-limiting guidelines should be considered in reading and interpreting the description of this invention set forth herein.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, an "oral care composition" is a composition that is suitable for administration or application to a human or animal subject for treating or preventing a condition of the oral cavity, or improving the hygiene and/or appearance of the subject.

As used herein, the term "dentifrice" refers to a paste, gel, or liquid formulation suitable for administration or application to the oral cavity.

Unless otherwise specified, all percentages and amounts expressed herein and elsewhere in the specification should be understood to refer to percentages by weight. The amounts given are based on the active weight of the material. The recitation of a specific value herein, whether referring to respective amounts of components, or other features of the embodiments, is intended to denote that value, plus or minus a degree of variability to account for errors in measurements. For example, an amount of 10% may include 9.5% or 10.5%, given the degree of error in measurement that will be appreciated and understood by those having ordinary skill in the art. All measurements are made at 25° C., unless otherwise specified.

In some embodiments the micro efficacy of a fluoride free and anionic surfactant free oral care composition are maintained at a high level by using a humectant system comprising glycerin, propylene glycol, and sorbitol. The micro efficacy of a composition is the ability of the composition to withstand growth of microorganisms. One method to test the micro efficacy level of a composition is through a rapid challenge test. The challenge test provides an early evaluation of a formula's ability to withstand incidental microbial challenge in a controlled manufacturing facility.

The rapid efficacy level test (challenge test) is conducted on a dentifrice to determine a test value, which represents that ability of the dentifrice to withstand the growth of bacteria. In order to demonstrate that a dentifrice is effective, a mixed pool of bacteria (Gram negative and Gram positive cocci) is introduced in the tested product and recovered over various time intervals. This test measures the rate of kill over time and the total kill over 24 hours. Results are calculated as Normalized Area Under the Curve (NAUC).

Fluoride ion sources and anionic surfactants, such as sodium lauryl sulfate, are main contributors to the micro efficacy of oral care compositions. Commercial fluoride free and anionic surfactant free dentifrices have NAUC values ranging from 17.0 to 30.0.

An oral care composition comprising glycerin, propylene glycol, and sorbitol according to the present invention has a NAUC value of greater than 30. In a preferred embodiment, the oral composition has a NAUC value of 65-75 or more. Without wishing to be bound by any particular theory of operation, the present inventors believe the high micro efficacy level according to the embodiments are due to the low water content of the compositions. Additionally, the existing water molecules in the embodiments are bound or made unavailable which aids in inhibiting the growth of microorganisms. As a consequence, it is preferred that the compositions of the invention contain less than 15% water, more preferably less than 12% water, even more preferably less than 10% water, based on the entire weight of the composition.

Glycerin may be present in the oral care composition in an amount within the range of from 10% to 35%, more preferably, from 17% to 33%, even more preferably from 19% to 29% by weight. In one preferred embodiment, the composition contains from 20% to 24% by weight glycerin.

Propylene glycol may be present in the oral care composition in an amount from 15% to 45%, more preferably from 19% to 35%, and even more preferably from 20% to 30% by weight. In one preferred embodiment, the composition contains about 25% by weight propylene glycol.

Sorbitol may be present in the oral care composition in an amount from 10% to 35%, more preferably from 17% to 30%, even more preferably from 18% to 28% by weight. In one preferred embodiment, the composition contains about 23% by weight sorbitol.

The present inventors further discovered that the addition of a pH control agent to a fluoride free and anionic surfactant free oral care composition having a humectant system comprising glycerin, propylene glycol, and sorbitol surprisingly increases the challenge test level of the composition to a level equivalent to traditional dentifrice systems.

In one embodiment, the pH control agent may be present in the oral care composition in an amount from about 0.05% to about 0.2% by weight. In a preferred embodiment, the composition contains about 0.1% pH control agent. In one embodiment, the pH control agent is citric acid.

The oral care composition comprising a pH control agent and a humectant system according to the present invention preferably has a NAUC value of greater than 1

The inventors have found that use of certain solvents or alcohol, and/or the use of greater than 35% glycerin and/or less than 17% by weight propylene glycol provide oral care compositions having NAUC less than 50.0, even less than 30.0.

Optional additives for the oral care compositions of the present invention may also be used, such as those commonly used for forming a dentifrice, including but not limited to: abrasives and/or amorphous silica, other humectants, stabilizing agents, antibacterial agents, sweeteners, colorants, healing agents, caries preventative agents, chelating/sequestering agents, vitamins, amino acids, proteins, anti-plaque agents, anti-calculus agents, opacifiers, antibiotics, anti-enzymes, enzymes, pH control agents, oxidizing agents, antioxidants, whitening agents, basic amino acids (in free base or salt form) and other pH control agents.

In one embodiment, the oral care composition may include flavorings or sweetening materials. Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillatrine, AMP (aspartyl phenyl alanins, methyl ester), saccharine and the like. Suitably, flavor and sweetening agents may each or together comprise from about 0.001% to 5% or more of the preparation, each being typically about 0.1-2.5%.

In certain embodiments, the oral care composition may comprise zwitterionic and non-ionic surfactants. Zwitterionic surfactants are known in the art, and generally include surfactants which are neutrally charged overall, but carry at least one positive charged atom/group, and at least one negatively charged atom/group. Preferable zwitterionic surfactants used in the present invention are quaternary ammonium compounds and betaines, e.g, amido betaines, such as cocoamidoethyl betaine, cocoamidopropyl betaine, lauramidopropyl betaine and the like. In some embodiments, the zwitterionic surfactant for use in the present invention is cocoamidopropyl betaine.

Non-ionic surfactants are known in the art, and generally include surfactants which are not electrically charged. A preferred nonionic surfactant may be poly(oxyethylene)-poly(oxypropylene) block copolymers. Such copolymers are known commercially by the non-proprietary name of poloxamers. The name poloxamer is often used in conjunction with a numeric suffix to designate the individual identification of each copolymer. Poloxamers may have varying contents of ethylene oxide and propylene oxide which results in poloxamers which have a wide range of chemical structures and molecular weights. A preferred poloxamer is Poloxamer 407, sold under the trade name PLURONIC F127 by BASF, Inc. (Parsippany, N.J.).

In various embodiments, the oral care composition may include thickeners, gelling agents or combinations thereof. Thickeners or gelling agents useful herein include inorganic, natural or synthetic thickeners or gelling agents. Examples of thickeners and gelling agents useful herein include inorganic thickening silicas such as: an amorphous silica, for example Zeodent® 165 (Huber Corporation); Irish moss; iota-carrageenan; gum tragacanth; polyvinylpyrrolidone; glycerites; gums such as tragacanth, ghatti, acacia, veegum; sodium alginate; carboxymethyl cellulose; hydroxyethyl cellulose, hydroxypropyl cellulose; hydroxymethyl cellulose; hydroxymethyl carboxypropyl cellulose; methyl cellulose; ethyl cellulose; sulfated cellulose; as well as mixtures and combinations of these compounds. In certain embodiments, the composition comprises a polishing agent, such as a silica, a calcined alumina, sodium bicarbonate, calcium carbonate, dicalcium phosphate or calcium pyrophosphate.

It is preferred that the compositions of the invention do not contain alcohol or other solvents, not only because the compositions are intended for use by children, but also because certain of the alcohols and solvents decrease the NAUC value. For example, use of polyethylene glycol (PEG) and/or xylitol decreases the NAUC value to below 47.0.

In various embodiments, the present invention provides methods for providing oral health benefits to an oral surface, comprising contacting compositions according to embodiments of the present invention to the oral surface.

The embodiments described herein can be further understood by reference to the following non-limiting examples.

EXAMPLES

Example 1

Table 1 illustrates a formulation according to an embodiment of the invention. The efficacy of Formula 1 was tested in a challenge test, resulting in a NAUC value of 88.51.

TABLE 1

| Formula 1 | |
|---|---|
| Ingredient | Weight Percent |
| Sorbitol | 23.0 |
| Glycerin | 20.0 |
| Propylene glycol | 25.0 |

TABLE 1-continued

| Formula 1 | |
|---|---|
| Ingredient | Weight Percent |
| Saccharin | 0.25 |
| Poloxomer 407 | 2.0 |
| CMC 7MF | 0.5 |
| Zeodent 165 | 10.0 |
| Zeodent 114 | 10.0 |
| Water | 9.0 |
| Flavor | 0.25 |

Example 2

Table 2 illustrates another formulation according to an embodiment of the invention. The efficacy of Formula 2 was tested in a challenge test resulting in a NAUC value of 133.31, equivalent to the test value of traditional dentrifices that include fluoride ion sources and anionic surfactants.

TABLE 2

| Ingredient | Weight Percent |
|---|---|
| Sorbitol | 23.0 |
| Glycerin | 24.0 |
| Propylene glycol | 25.0 |
| Saccharin | 0.25 |
| Poloxomer 407 | 2.0 |
| CMC 7MF | 0.5 |
| Zeodent 165 | 8.0 |
| Zeodent 114 | 8.0 |
| Water | 8.9 |
| Flavor | 0.25 |
| Citric Acid | 0.1 |

As will be seen below, Formula 2 is the same as Formula 4 in Table 3 below, expect 0.1 wt % citric acid was added (and the amount of water decreased). The addition of citric acid unexpectedly raised the NAUC value from 61.31 to 133.31, more than doubling its value.

Example 3

Table 3 illustrates a series of formulations according to various embodiments of the invention. The efficacy of the formulas were tested in accordance with the challenge test resulting in a NAUC value of greater than 50.0.

TABLE 3

| | Amount of Ingredient (wt %) | | | | |
|---|---|---|---|---|---|
| Ingredient | Formula 3 | Formula 4 | Formula 5 | Formula 6 | Formula 7 |
| Sorbitol | 18.0 | 23.0 | 19.3 | 19.3 | 19.3 |
| Glycerin | 20.0 | 24.0 | 24.0 | 24.0 | 24.0 |
| Propylene glycol | 30.0 | 25.0 | 29.0 | 29.0 | 29.0 |
| Saccharin | 0.25 | 0.25 | 0.25 | 0.25 | 0.25 |
| Poloxomer 407 | 2.0 | 2.0 | 2.0 | 2.0 | 2.0 |
| CMC 7MF | 0.5 | 0.5 | 0.5 | 0.5 | 0.5 |
| Zeodent 165 | 10.0 | 8.0 | 8.0 | 8.0 | 8.0 |
| Zeodent 114 | 10.0 | 8.0 | 8.0 | 8.0 | 8.0 |
| Water | 8.98 | 8.98 | 8.98 | 8.98 | 8.98 |
| Flavor | 0.25 | 0.25 | 0.01 | 0.02 | 0.02 |
| Color | | 0.038 | 0.038 | 0.038 | 0.038 |
| NAUC Value | 71.74 | 61.31 | 56.98 | 59.62 | 53.42 |

Comparative Examples

Table 4 illustrates a series of formulations according to various comparative embodiments of the invention, in which either PEG or xylitol, or both were used, or where the amount of glycerin is greater than 35 and/or the amount of propylene glycol is less than 17. Some of the comparative examples also utilized tetrasodium pyrophosphate (TSPP). The efficacy of the formulas were tested in accordance with the challenge test resulting in a NAUC value of less than 50.0.

TABLE 4

| | Amount of Ingredient (wt %) | | | | | | |
|---|---|---|---|---|---|---|---|
| Ingredient | A | B | C | D | E | F | G |
| Sorbitol | 20.0 | 20.0 | 23.0 | 23.0 | 23.0 | 23.0 | 23.0 |
| Glycerin | 35.7 | 35.32 | 20.0 | 20.0 | 20.0 | 17.0 | 20.0 |
| Propylene glycol | 15.0 | 15.0 | 25.0 | 25.0 | 25.0 | 25.0 | 25.0 |
| Saccharin | 0.15 | 0.15 | 0.15 | 0.15 | 0.15 | 0.15 | 0.15 |
| Poloxomer 407 | 2.0 | 2.0 | 2.0 | 2.0 | 2.0 | 2.0 | 1.0 |
| CMC 7MF | 0.5 | 0.5 | 0.5 | 0.5 | 0.5 | 0.5 | 0.5 |
| Zeodent 165 | 8.0 | 8.0 | 8.0 | 8.0 | 8.0 | 8.0 | 10.0 |
| Zeodent 114 | 8.0 | 8.0 | 9.3 | 9.3 | 9.3 | 9.3 | 10.0 |
| Water | 10.0 | 10.0 | 8.98 | 8.98 | 5.98 | 8.98 | 8.98 |
| Flavor | 0.1 | 0.03 | 0.03 | 0.03 | 0.03 | 0.03 | 0.03 |
| Color | 0.38 | | | | | | |
| TSPP | 0.5 | 1.0 | | | | | |
| PEG | | | 3.0 | | 3.0 | 3.0 | 1.3 |
| Xylitol | | | | 3.0 | 3.0 | 3.0 | |
| NAUC Value | 23.93 | 25.65 | 33.87 | 33.04 | 46.45 | 34.42 | 34.66 |

It is intended that each patent, application, and printed publication, mentioned in this patent document be hereby incorporated by reference in its entirety.

As those skilled in the art will appreciate, numerous changes and modifications may be made to the embodiments described herein, without departing from the spirit of the invention. It is intended that all such variations fall within the scope of this invention.

The invention claimed is:

1. An oral care composition comprising:
    from 15% to 35% by weight glycerin;
    from 17% to 45% by weight propylene glycol;
    from 15% to 35% by weight sorbitol; and
    from 0.05% to 0.4% by weight citric acid;
   wherein the composition is free of anionic surfactants and a fluoride ion source, and wherein the composition comprises less than 15% water, based on the entire weight of the composition.

2. The composition of claim 1, wherein the composition comprises 0.1% w/w citric acid.

3. The composition of claim 1, wherein glycerin comprises 18% to 30% by weight of the oral care composition.

4. The composition of claim 1, wherein glycerin comprises 20% to 25% by weight of the oral care composition.

5. The composition of claim 1, wherein the propylene glycol comprises 20% to 35% by weight of the oral care composition.

6. The composition of claim 1, wherein the propylene glycol comprises 24% to 32% by weight of the oral care composition.

7. The composition of claim 1, wherein the propylene glycol comprises about 25% by weight of the oral care composition.

8. The composition of claim 1, wherein the sorbitol comprises 18% to 28% by weight of the oral care composition.

9. The composition of claim 1, wherein the sorbitol comprises 23% by weight of the oral care composition.

10. An oral care composition comprising:
from 20% to 24% by weight glycerin;
about 25% by weight propylene glycol;
about 23% by weight sorbitol;
about 0.1% by weight citric acid; and
wherein the composition is free of anionic surfactants and a fluoride ion source, and wherein the composition comprises less than 15% water, based on the entire weight of the composition.

11. The composition of claim 10, wherein, when the composition is subjected to a challenge test by: introducing a mixed pool of bacteria (Gram negative and Gram positive cocci) into the tested product; drawing samples from the resulting composition at intervals over 24 hours; quantifying the rate of kill of the bacteria pool population over the sampling interval to produce a data set; and calculating the value of the Normalized Area Under the Curve (NAUC) of the data set when graphed as rate of kill of the bacteria pool population over time, the NAUC value is greater than 50.

12. The composition of claim 10, wherein the composition does not contain xylitol or polyethylene glycol.

13. A method of treating or preventing a disease or condition of the oral cavity comprising contacting the oral surface of a subject in need thereof, with a composition according to claim 1.

14. The composition of claim 1, wherein the composition comprises less than 10% water, based on the entire weight of the composition.

15. The composition of claim 1, wherein the composition comprises a poly(oxyethylene)-poly(oxypropylene) block copolymer.

16. The composition of claim 10, wherein, when the composition is subjected to a challenge test by: introducing a mixed pool of bacteria (Gram negative and Gram positive cocci) into the tested product; drawing samples from the resulting composition at intervals over 24 hours; quantifying the rate of kill of the bacteria pool population over the sampling interval to produce a data set; and calculating the value of the Normalized Area Under the Curve (NAUC) of the data set when graphed as rate of kill of the bacteria pool population over time, the (NAUC) value is greater than 65.

17. The composition of claim 10, wherein, when the composition is subjected to a challenge test by: introducing a mixed pool of bacteria (Gram negative and Gram positive cocci) into the tested product; drawing samples from the resulting composition at intervals over 24 hours; quantifying the rate of kill of the bacteria pool population over the sampling interval to produce a data set; and calculating the value of the Normalized Area Under the Curve (NAUC) of the data set when graphed as rate of kill of the bacteria pool population over time, the NAUC value is greater than 75.

* * * * *